United States Patent
Ekanayake (10) Patent No.: US 7,222,519 B2
(45) Date of Patent: May 29, 2007

(54) SOIL MOISTURE CONTENT MEASUREMENT SYSTEM AND METHOD

(75) Inventor: Jagath Chandralal Ekanayake, Lincoln (NZ)

(73) Assignee: Landcare Research New Zealand Limited, Lincoln (NZ)

( * ) Notice: Subject to any disclaimer, the term of this patent is extended or adjusted under 35 U.S.C. 154(b) by 404 days.

(21) Appl. No.: 10/518,282

(22) PCT Filed: Jun. 17, 2003

(86) PCT No.: PCT/NZ03/00122

§ 371 (c)(1),
(2), (4) Date: Dec. 16, 2004

(87) PCT Pub. No.: WO03/106996

PCT Pub. Date: Dec. 24, 2003

(65) Prior Publication Data

US 2005/0218244 A1    Oct. 6, 2005

(30) Foreign Application Priority Data

Jun. 17, 2002   (NZ) .................................... 519609

(51) Int. Cl.
*G01N 25/56* (2006.01)
(52) U.S. Cl. .......................................................... 73/73
(58) Field of Classification Search ..................... 73/73
See application file for complete search history.

(56) References Cited

U.S. PATENT DOCUMENTS

| | | | |
|---|---|---|---|
| 2,545,281 A * | 3/1951 | Hunt | 73/73 |
| 3,968,428 A | 7/1976 | Numoto | |
| 4,068,525 A | 1/1978 | Skaling | |
| 4,197,866 A | 4/1980 | Neal | |
| 4,266,878 A | 5/1981 | Auer | |
| 4,341,112 A | 7/1982 | Mackay et al. | |
| 4,655,076 A | 4/1987 | Weihe et al. | |
| 4,929,885 A | 5/1990 | Dishman | |
| 5,038,040 A | 8/1991 | Funk et al. | |

(Continued)

FOREIGN PATENT DOCUMENTS

JP         11-201890         7/1999

(Continued)

OTHER PUBLICATIONS

Sirotkin V.V., Derwent Abstract Accession, Abstract and Drawing, SU 1807340 A1, No. 94-190806/23, Apr. 7, 1993.

*Primary Examiner*—Hezron Williams
*Assistant Examiner*—Rodney Frank
(74) *Attorney, Agent, or Firm*—Marshall, Gerstein & Borun LLP (57) ABSTRACT

The invention provides a soil moisture content measurement system comprising a porous plate arranged to support a soil sample; a hanging water tube extending downwardly from the porous plate, the tube arranged to convey liquid toward and away from the porous plate; a measuring capillary tube in connection with the hanging water tube, the measuring capillary tube arranged to convey liquid toward and away from the hanging water tube; measurement apparatus configured to measure the movement of liquid within the measuring capillary tube; and a data memory configured to receive and store data from the measurement apparatus representing liquid movement measurements within the measuring capillary tube. The invention also provides a related method of measuring soil moisture content.

16 Claims, 9 Drawing Sheets

U.S. PATENT DOCUMENTS

| | | |
|---|---|---|
| 5,072,981 A | 12/1991 | Weaver et al. |
| 5,073,756 A | 12/1991 | Brandelik |
| 5,887,491 A | 3/1999 | Monson et al. |
| 5,898,310 A | 4/1999 | Liu |
| 6,013,158 A * | 1/2000 | Wootten .................. 202/99 |
| 6,044,324 A | 3/2000 | Boerhave et al. |
| 6,215,317 B1 | 4/2001 | Siddiqui et al. |
| 6,234,008 B1 | 5/2001 | Sjoblom et al. |
| 6,938,461 B1 * | 9/2005 | Johnson ..................... 73/38 |

FOREIGN PATENT DOCUMENTS

| | | |
|---|---|---|
| RU | 877371 | 10/1981 |
| RU | 1247748 A1 | 7/1986 |
| RU | 1755190 A1 | 8/1992 |
| RU | 2102721 C1 | 1/1998 |

\* cited by examiner

| Water volume in/out from the sample & programme data output from J & J ||||||
|---|---|---|---|---|---|
| Time | Volume Out / IN ml | Suction applied cm water | Equilibrium Time Limit min | Saturating Drying or Wetting | Cycle Number |
| 6 | 40 | 0 | 1 | 1 | 0 |
| 11 | 80 | 0 | 1 | 1 | 0 |
| 16 | 120 | 0 | 1 | 1 | 0 |
| 22 | 160 | 0 | 1 | 1 | 0 |
| 27 | 200 | 0 | 1 | 1 | 0 |
| 33 | 240 | 0 | 1 | 1 | 0 |
| 39 | 280 | 0 | 1 | 1 | 0 |
| 45 | 320 | 0 | 1 | 1 | 0 |
| 52 | 360 | 0 | 1 | 1 | 0 |
| 59 | 400 | 0 | 1 | 1 | 0 |
| 66 | 440 | 0 | 1 | 1 | 0 |
| 73 | 480 | 0 | 1 | 1 | 0 |
| 81 | 520 | 0 | 1 | 1 | 0 |
| 89 | 560 | 0 | 1 | 1 | 0 |
| 97 | 600 | 0 | 1 | 1 | 0 |
| 105 | 640 | 0 | 1 | 1 | 0 |
| 114 | 680 | 0 | 1 | 1 | 0 |
| 124 | 720 | 0 | 1 | 1 | 0 |
| 134 | 760 | 0 | 1 | 1 | 0 |
| 144 | 800 | 0 | 1 | 1 | 0 |
| 155 | 840 | 0 | 1 | 1 | 0 |
| 167 | 880 | 0 | 1 | 1 | 0 |
| 180 | 920 | 0 | 1 | 1 | 0 |
| 193 | 960 | 0 | 1 | 1 | 0 |
| 208 | 1000 | 0 | 1 | 1 | 0 |
| 224 | 1040 | 0 | 1 | 1 | 0 |
| 241 | 1080 | 0 | 1 | 1 | 0 |
| 259 | 1120 | 0 | 1 | 1 | 0 |

SOIL MOISTURE CONTENT MEASUREMENT SYSTEM AND METHOD

RELATED APPLICATIONS

This application is a National Stage application of PCT/NZ03/00122 filed Jun. 17, 2003, which claims priority from New Zealand Patent Application No. 519609 filed Jun. 17, 2002.

FIELD OF INVENTION

The invention relates to an automated system and method for obtaining soil moisture content data to estimate moisture release curves, particularly designed to obtain drying and wetting water release curves for an undisturbed or remoulded soil sample.

BACKGROUND TO INVENTION

One of the most important soil physical relationships requiring estimation is the amount of water available in the soil represented by a water retention curve. A water retention curve represents the relationship between soil water tension (matric potential) and soil water content of the soil. Many models have been developed to estimate the amount of water available in soil from small farmlands to large-scale catchments. The soil water retention curve plays a major role in many of these models. Studies of water balance and runoff generation leading to sediment production require the calculation of a soil water retention curve at the lower end (0 to 100 cm soil water tension).

The most popular and only reliable method to obtain the soil water retention curve at the lower tension is a tension plate with a hanging water column. This method has been in use for over 70 years. A tension plate is made from a porous material such as ceramic or a sand bed. Since larger pore space dominates the soil water characteristics at the lower tension range, tests must be carried out with either minimum or no disturbance to the soil sample.

To use the tension table, the soil sample must first be saturated. During saturation, the weight of the soil sample is checked regularly to find the equilibrium point. Once the saturation process is completed, different tensions are applied to the soil sample, which sits on the tension plate, by the hanging water column. In order to find the equilibrium point for each applied tension, the water meniscus in the hanging water column is monitored regularly. This is a very time consuming task. Once the soil sample reaches equilibrium, it is transferred to a weighing apparatus at the end of each tension step to estimate the moisture content.

The main disadvantages of this method are:
1. Disturbance to the fragile soil matrix (larger pore structure) due to regular handling of the soil sample.
2. Inaccurate soil moisture estimation due to sample handling.
3. High labour intensity. Regular supervision is necessary to determine the equilibrium points.

It would be useful to at least partially automate the test procedure to eliminate or reduce the drawbacks. An added advantage of an automated system could be the ability to produce accurate outflow data to estimate the unsaturated hydraulic conductivity.

SUMMARY OF INVENTION

In broad terms in one form the invention comprises a soil moisture content measurement system comprising a porous plate arranged to support a soil sample; a hanging water tube extending downwardly from the porous plate, the tube arranged to convey liquid toward and away from the porous plate; a measuring capillary tube in connection with the hanging water tube, the measuring capillary tube arranged to convey liquid toward and away from the hanging water tube, the measuring capillary tube arranged to be raised and/or lowered with respect to the soil sample; measurement apparatus configured to measure the movement of liquid within the measuring capillary tube; and a data memory configured to receive and store data from the measurement apparatus representing liquid movement measurements within the measuring capillary tube.

In broad terms in another form the invention comprises a method of measuring a moisture retention curve of a soil sample comprising the steps of supporting a soil sample on a porous plate; positioning the height of a measuring capillary tube with respect to the porous plate to enable liquid to be conveyed between the measuring capillary tube and the porous plate; positioning a hanging water tube to convey liquid between the porous plate and the measuring capillary tube; performing at least one purging cycle in which liquid is introduced into the measuring capillary tube and the soil sample; performing at least one drying cycle in which the measuring capillary tube is substantially emptied of liquid, liquid is permitted to travel from the soil sample through the porous plate to the measuring capillary tube, and the movement of liquid within the measuring capillary tube is measured; storing in computer memory data representing liquid movement measurements within the measuring capillary tube; and calculating the moisture retention curve from the data representing liquid movement measurements.

BRIEF DESCRIPTION OF THE FIGURES

Preferred forms of the moisture release curve calculation system and method will now be described with reference to the accompanying Figures in which.

DETAILED DESCRIPTION OF PREFERRED FORMS

Figure 1:
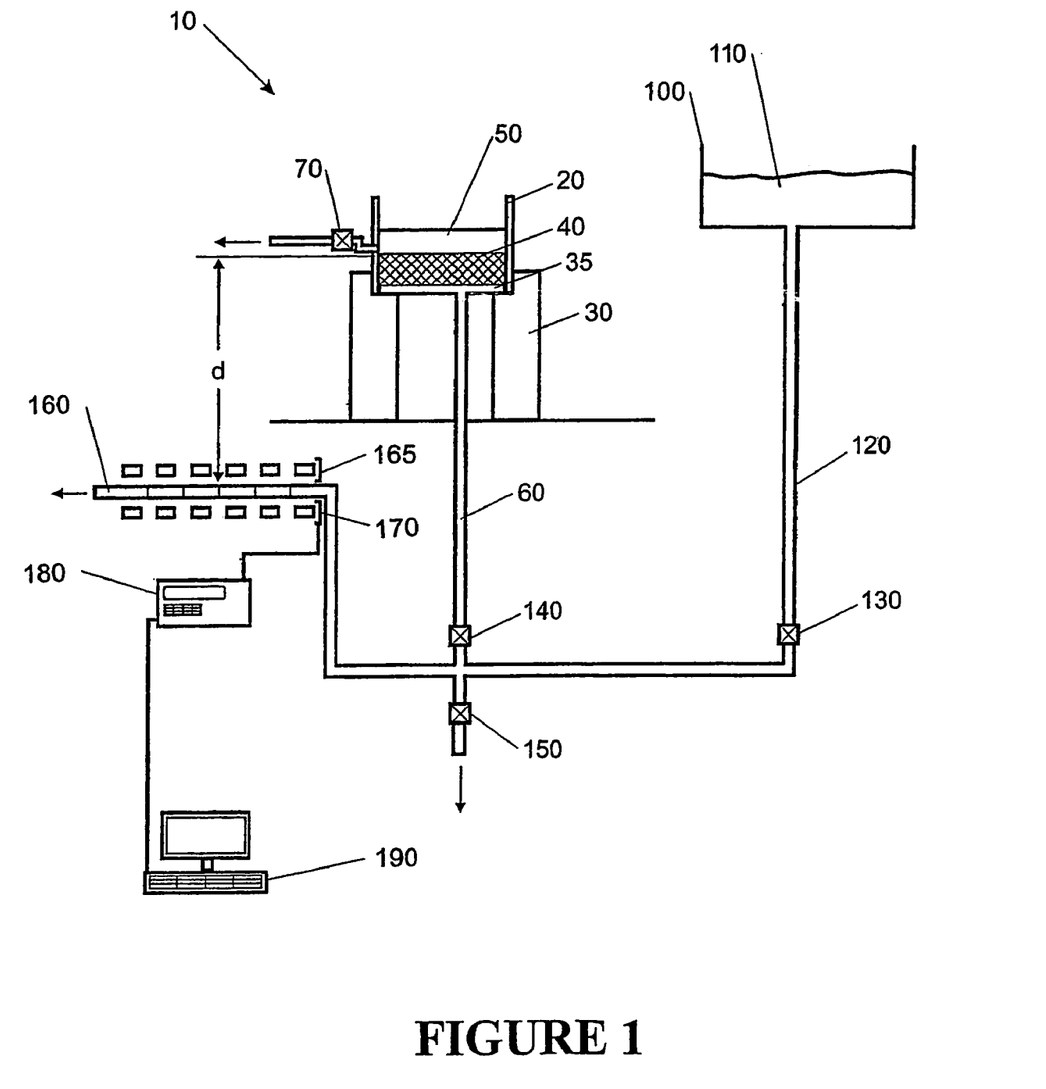
FIG. 1 is a preferred form system of the invention.

FIG. 1 shows a schematic representation of one form of the invention 10. A soil sample retaining ring 20 is positioned on a porous plate 40 which is rigidly connected to a sealed water reservoir 35. The porous plate 40 and the water reservoir beneath it, rests on the structural support or base 30, as a single unit. The porous plate is constructed of a suitable material that is permeable to liquid such as water, and is preferably of a high flow type with an air entry value of 0.5 bar. The soil sample retaining ring 20 is preferably supported on the porous plate 40, and the join between the soil sample retaining ring 20 and porous plate 40 is coated with a suitable water impermeable material such as silicon grease in order to ensure a proper seal between the soil sample retaining ring and the porous plate.

The retaining ring 20 contains the undisturbed or remoulded soil sample 50 for which a moisture release curve is desired. Inside the sealed water reservoir 35 a channel is formed in a shape of a spiral. Extending downwardly from one end of the spiralled channel in the sealed water reservoir below the porous plate 40 is a hanging water tube 60. This tube is arranged to convey liquid, for example water, upwardly toward and through the porous plate 40 where required and to convey water away from the porous plate 40 where required. An air valve 70 fitted at the other end of the spiral shaped channel in the water reservoir releases any air trapped in the tubes through the air valve 70 during a purging cycle as described below.

A water receptacle or tank 100 containing a liquid such as water 110 supplies de-aired water to the rest of the system 10 through a supply tube 120. This de-aired water 110 is used to fill the hanging water tube 60 and a measuring capillary tube described below, which saturates the soil sample 50. The water tank 100 is preferably elevated with respect to the soil sample 50 to exert sufficient pressure difference to force the water from the tank 100 through the sealed water reservoir 35 and porous plate 40 to the soil sample. The water supply tube 120 is preferably fitted with a suitable tank valve 130 to control the flow of water exiting the tank 100 to the rest of the system.

The hanging water tube 60 is also fitted with a suitable sample valve 140 to control the flow of water from the water tank 100 travelling into and up the hanging water tube 60, and to control the flow of water exiting the tube 60. A drain valve 150 is arranged to control the flow of water out of the supply tube 120 and the hanging water tube 60.

A measuring capillary tube 160 is connected to the ends of the hanging water tube 60 and the supply tube 120. The horizontal measuring tube 160 is vertically positioned with respect to the soil sample 50 by a distance "d" in order to apply tension to the soil sample 50. It is envisaged that the distance "d" can be varied in order to alter the applied soil water tension on the soil sample 50. The distance "d" could be varied by enabling the measuring tube 160 to be raised and lowered with respect to the soil sample 50 using a stepper motor (not shown) in order to apply different soil water tensions to the soil sample.

The measuring capillary tube 160 is preferably substantially horizontal and parallel to the porous plate 40 and is fitted with measurement apparatus to measure the displacement of water along the tube 160 in either direction. It will be appreciated that the measuring capillary tube could be positioned substantially vertically or alternatively could be positioned at any angle to the horizontal.

In one form, the measurement apparatus includes a series of infrared emitters 165 positioned on one side of the measurement tube 160, together with a series of corresponding infrared detectors 170. The emitters 165 and detectors 170 are preferably arranged as corresponding pairs. Modulated infrared beams at 40 kHz are transmitted from the infrared emitters 165 to the infrared detectors 170 through the measurement tube 160.

It is envisaged that part of the measuring tube 160 will contain water and that a meniscus appears at the intersection between the part of the tube 160 filled with water and the part of the tube that does not contain water. The meniscus will travel along the measuring tube 160 as water enters or exits the tube 160.

Each pair of emitters and detectors preferably defines a segment of the measuring tube 160; the amount of water in each segment is pre-determined. Each segment could hold, for example, 0.1 ml of water. The meniscus described above will obscure the infrared beams as it passes between an emitter/detector pair and so indicate the direction of water movement and the number of water filled segments and hence volume in the measuring tube 160.

The horizontal measuring tube can be withdrawn for cleaning or can be replaced with a smaller diameter measuring tube 160 to increase the resolution as desired.

The system 10 further comprises a hardware user interface 180, which is configured to receive, process and store data from the measuring tube 160 and to control the rest of the system according to instructions from the user interface 180. The device includes a data memory configured to store data and could have an associated microprocessor or microcontroller. The hardware user interface 180 includes a suitable data port to which a personal computer, workstation, or other programmable device 190 can be connected. The computer 190, running appropriate software, sends the required configuration to the hardware user interface to perform the test. The computer 190 is also configured to receive data stored in the micro controller and to process and to generate a series of moisture release curves for the soil sample 50.

Figure 2:
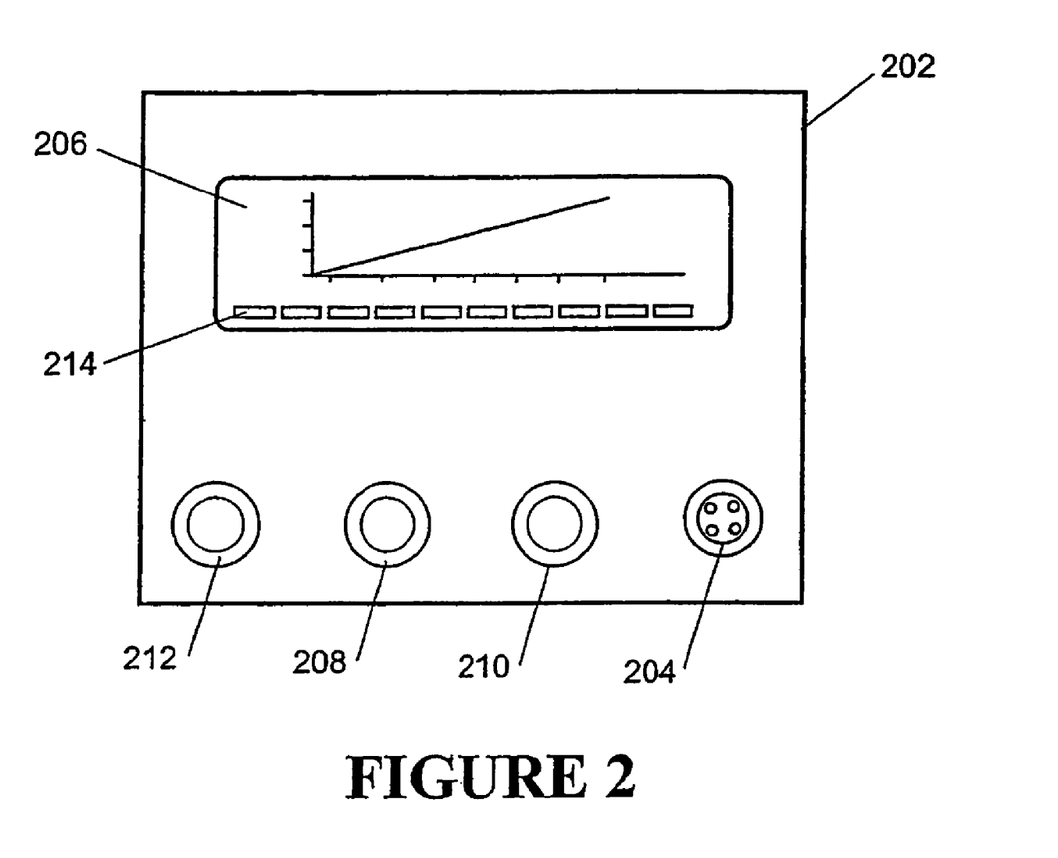
FIG. 2 shows a hardware user interface apparatus forming part of the system of FIG. 1.

FIG. 2 shows the front panel of one form of the hardware user interface 180. The hardware is preferably connected to a power supply using a 12-volt line.

The hardware user interface 180 could include a pilot light 202 showing the status and current operation of the system, and an RS232 serial port 204 for connection to a personal computer or workstation. The hardware user interface could also be provided with a graphical liquid crystal display (GLCD) 206 for displaying instructions, current progress of the saturation wetting/drying cycles in graphical form as water in/out against time, and program details.

The apparatus also includes several button controls, for example 'Bypass the current tension step' 208, 'Start the test' 210, and 'activate the Display' 212. The functions of these controls are described below.

The display 206 on the hardware user interface 180 could further include a series of LED displays 214. The number of LED displays illuminated indicates the number of water segments in the measuring tube 160 from FIG. 1 that are full of water. For example, if 4 LED displays are illuminated, then 4 segments in the measuring tube 160 are full of water, with each segment containing approximately 0.1 ml of water.

In order to obtain drying and wetting moisture release curves of a soil sample, the system 10 from FIG. 1 is placed through one or more purging, drying, and wetting cycles.

The intention of the purging cycle is to remove air bubbles from the tubes 60, 120, 160, the porous plate 40, and the water reservoir 35. Referring to FIG. 1, the distance "d" is minimised by, for example, raising the measuring tube 160 to an upper limit. The valves 140 & 150 are closed and the valve 130 is opened to fill the measuring tube 160 with de-aired water from tank 100. Then the valves 140 and 70 are opened and valve 130 closed, allowing water and trapped air bubbles in the tubes to flow through the tube 60 along the spiralled water channel in the sealed water reservoir 35 to escape through the air valve 70.

It is envisaged that this purging process be repeated 20 times or in any case enough times so that the water volume through the system is replaced in all the tubes.

Following the purging cycle, a drying cycle imposes a tension on the soil sample 50 by lowering the measuring tube 160 to a height corresponding to the tension required to remove water from the soil sample. The measuring tube 160 is first emptied, by opening the valve 150 leaving all other valves closed. Valve 150 is closed as soon as the water meniscus inside the measuring tube 160 reaches the first infrared sensor at the right end of the measuring tube 160. With all other valves closed, the valve 140 is then opened to enable water released from the soil 50 to pass through the porous plate 40 down the hanging water tube 60 to the measuring tube 160.

As the water passes along the measuring tube 160, the water meniscus will trigger the emitter/detector pairs positioned along the measuring tube 160 and in this way, the direction of the water movement and the magnitude of the displacement of water along the measuring tube 160 is measured.

Water in the measuring tube 160 automatically drains from the tube when all segments in the measuring tube 160 are full of water. Computer 190 programmed by the user preferably controls all the activities of the system 10. It decides when to empty the measuring tube 160 by counting the number of active infrared receivers in the measuring tube. It drains the tube as the number of filled segments reaches a predefined maximum, for example 6, during a drying or purging cycle. It re-fills the measuring tube as the number of active segments reaches zero during a wetting cycle.

Computer 190 records the active segment number in real time as the water meniscus passes between each infrared beam. In this way, the amount of water taken up by the soil sample during a wetting cycle and the amount of water released by the soil sample 50 during drying can be estimated. The computer estimates the time elapsed since the water meniscus in the measuring tube 160 passes a segment and compares it with the pre-determined time limit. In one form, a user could specify a predetermined time limit for the water meniscus in the measuring tube 160 to move between two segments for each applied soil water tension. The time limit is the maximum time allowed for the water meniscus to travel between two segments under a given tension. If no water movement is detected in between two infrared beams in the measuring tube 160 during this predetermined time limit, the user could assume that the soil sample has reached equilibrium under the current tension.

Referring to FIG. 2, the user could press the Bypass button 208 to move onto the next cycle should the user decide that the predetermined time limit already programmed is too long. Alternatively, the system could be configured to move to the next cycle automatically as soon as the specified equilibrium time limit has been reached.

Once the drying cycle has been completed, a wetting cycle then starts (if programmed by the user) that enables the sample to absorb water from the measuring tube 160. The valves 140 and 150 are closed and the valve 130 opened to fill the measuring tube 160 with water 110 from the tank 100. The valve 130 is then closed and the valve 140 opened to enable the soil sample to take up water. As water travels along the measuring tube 160 and up the hanging water tube 60, the meniscus in the measuring tube 160 will travel along the measuring tube 160 and the movement of this meniscus will be tracked by the emitter/detector pairs. Once the measuring tube 160 is empty, the valve 140 is closed and the valve 130 opened to refill the measuring tube 160. The valve 130 is then closed and the valve 140 opened to resume water uptake by the soil sample 50. The user preferably sets a predetermined time limit. If no movement is measured along the measuring tube 160 during this predetermined time period, it is assumed that the soil 50 has reached equilibrium. Alternatively, the user could press the Bypass button 208 to complete the wetting cycle.

Computer 190 is preferably connected to the serial port 204 of the interface 180 to configure the system 10. Software running on the personal computer 190 provides a graphical user interface to control all the valves and movement of the measuring tube.

Figure 3:
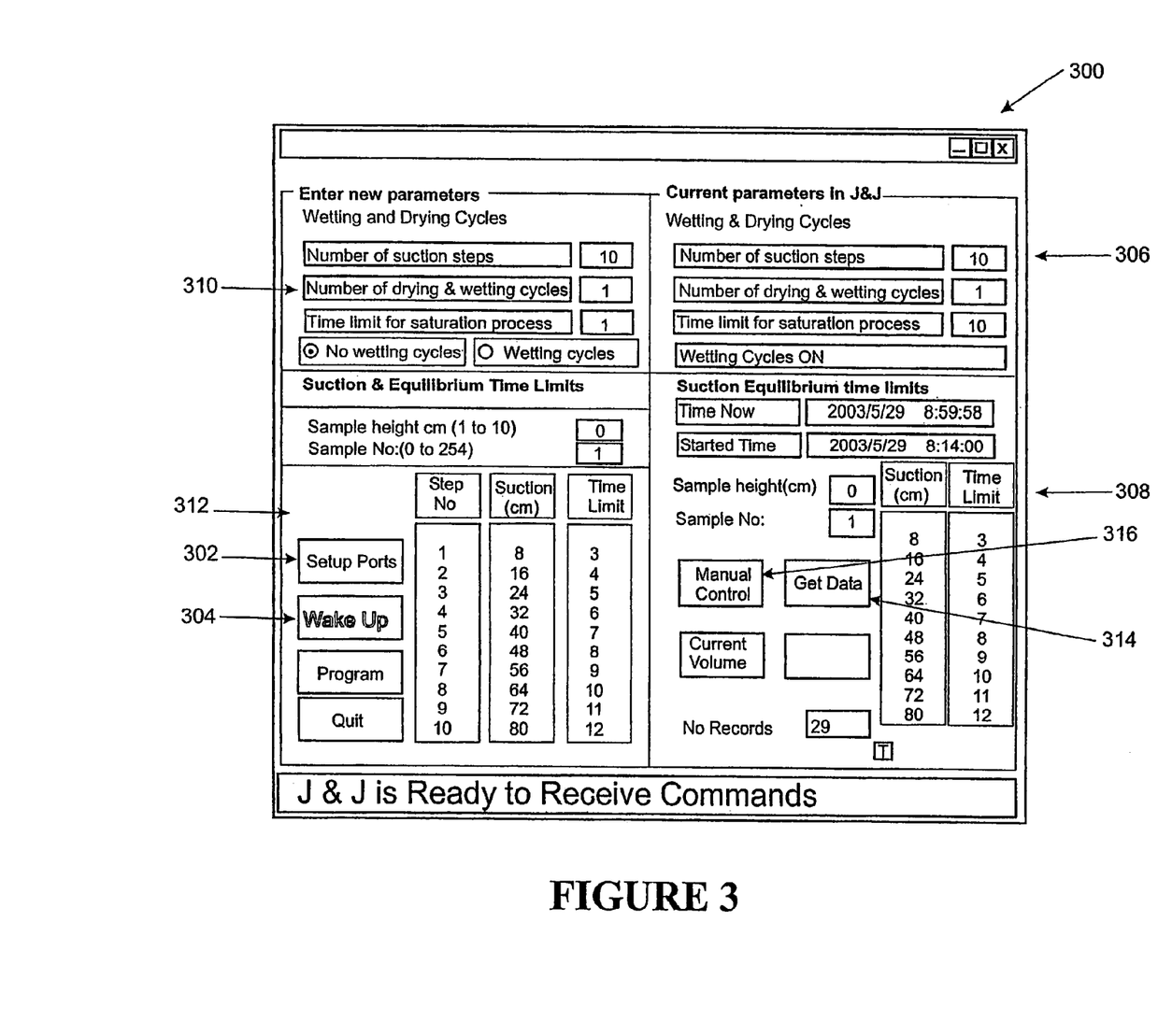
FIG. 3 shows a software user interface forming part of the system of FIG. 1.

FIG. 3 illustrates a preferred form graphical user interface 180 of software installed and operating on the computer 190. In use, the computer 190 is connected through a serial port to the hardware interface 180. Clicking on the Set up Ports and Files button 302 brings up the window shown in FIG. 4. The select port button enables a user to select the COM port on the computer and to specify the appropriate baud rate. The user could select, for example, a baud rate of 9,600.

Once the port is set up, Wake Up J&J button 304 is selected by the user to start data communication between the computer 190 and the hardware interface 180. Data are retrieved from the interface 180 in order to populate the Wetting and Drying Cycles panel 306 and the Suction Equilibrium time limits panel 308 that represent previously programmed values.

Using Wetting and Drying Cycles panel 310, the user specifies new parameters for a soil sample, using the previous values in panel 308 as a guide. In panel 460, the user may specify the number of drying and wetting cycles, the number of suction steps, and the time limit for the saturation process. Selecting the number '2' will result in two drying cycles and two wetting cycles for example. The user may specify the number of suction steps up to a maximum of 10. The suction steps are also referred to as tension steps. The user may also specify a predetermined time limit for the saturation process. A time of 1 minute means that the saturation process will be terminated if the soil sample does not cause one segment of movement (0.1 ml) in the measuring tube 160 during a 1-minute period. The user can also specify the soil sample height.

In panel 312, the user can specify, for each suction or tension step, a tension value and a time limit. The tension value represents the distance "d" between the soil sample 50 and the measuring tube 160. In this preferred form, the resolution of the suction is 1 mm and the maximum suction is 1000 mm. It is envisaged that the apparatus 180 controls distance "d" and this distance "d" is adjusted according to the suction steps specified in the user-entered program.

A four-phase unipolar stepper motor preferably controls the movement of the hanging water column, which then varies the suction applied to the soil sample.

The user is also able to specify three different time limits to determine the equilibrium status for a saturating, drying, and wetting cycle under a given tension. If the soil sample does not take one segment of water during the wetting process, or remove one segment of water during the drying process within the specified time limit for a particular step, then the system assumes that the soil sample has come to equilibrium under that tension value.

Once the user has entered the required data into the panels 310 and 312, data representing these parameters are transferred to the hardware interface 180, and the computer 190 is disconnected. After disconnecting the computer 190 from the interface 180, the system 10 undergoes several purging cycles to remove air bubbles from the system. The display 206 on the hardware interface 180 tells the user that the system is being purged. The display could also show the user the purging cycle number currently being performed by the system.

Once the system is purged, the soil sample is placed on the porous plate 40 and the Start button 210 pressed to initiate the first drying cycle and/or the whole experiment. The display could indicate to the user whether the system is undergoing a drying or a wetting cycle, the applied tension in centimetres applied to the soil sample 50, the volume of water taken up or expelled from the soil sample in segments, and the total time elapsed to take or expel these segments.

The drying or wetting cycle continues until the equilibrium time limit specified by the user has been reached or the system has been bypassed with the user pressing the Bypass button 208.

The display is preferably a graphical liquid crystal display (GLCD) 206 programmed to turn off after a few minutes but restarted by the user pressing the Display button 212. The Display button 212 enables a user to select the required information window. For example, a single press of the Display button 212 will show the progress of the current suction step, pressing it twice will show the overall progress of the current cycle. Three presses of the Display button 212 will show the program details.

On completion, the display 206 reveals a test completion message. The user reconnects the computer 190 to the apparatus 180 and the "Wake-Up J&J" button 304 selected by the user.

Figure 5:
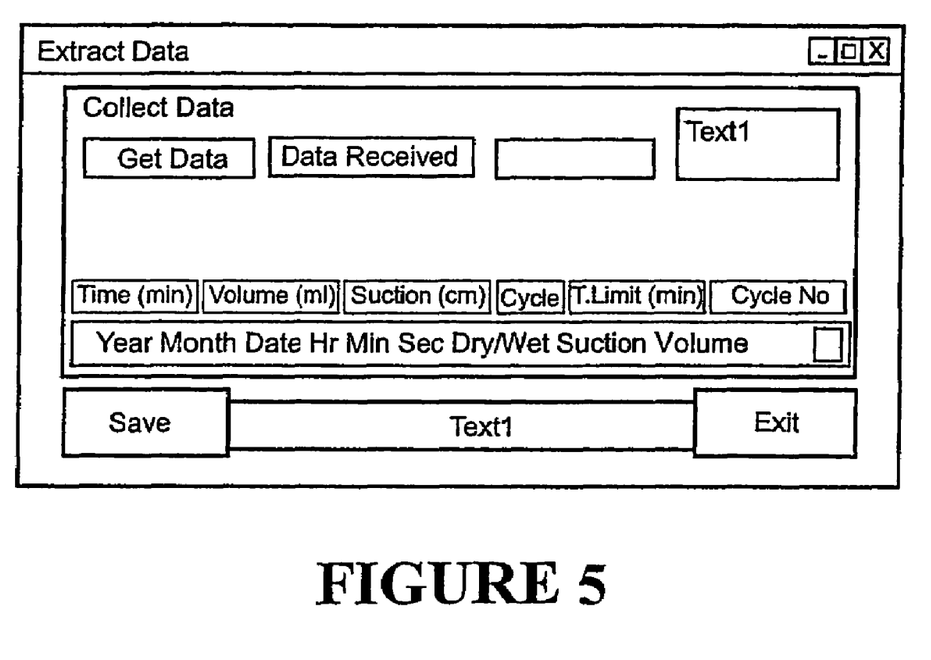
FIG. 5 shows a collect data window from the interface of FIG. 3.

Referring to FIG. 3, the user presses the "Get Data" button 314, which presents to the user the window shown in FIG. 5. The user then selects the "Get Data" button to start collecting data from the apparatus 180. The panel shows various text messages to the user guiding the user through the process of data collection.

Figure 4:
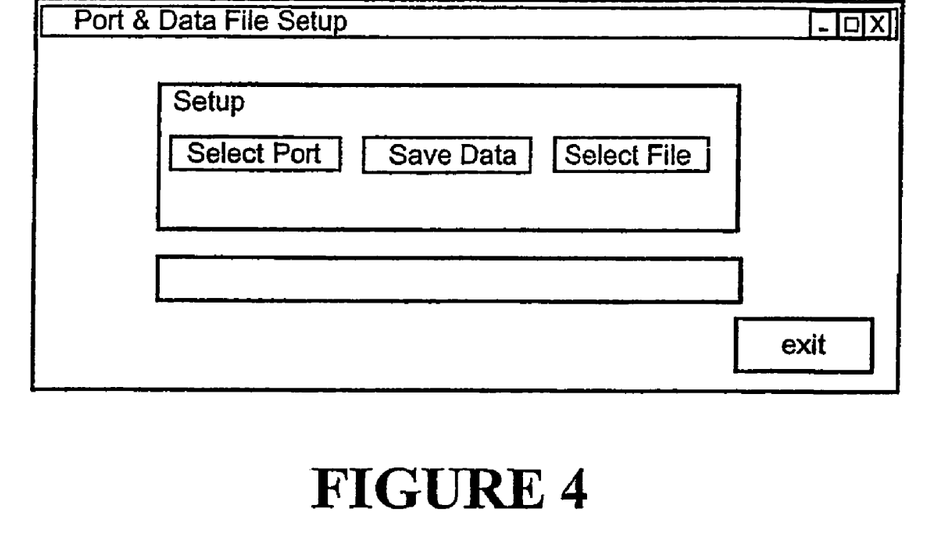
FIG. 4 shows a set up window from the interface of FIG. 3.

Once the user has collected the data from the micro controller, the user selects the "Set Up Ports & Files" button 302 and selects the "Select File" button shown in FIG. 4. The user may then specify a file name by which to index the data retrieved from the apparatus 180 using the "Save Data" button.

The downloaded data is preferably saved to an EXCEL file and the final moisture release curves are automatically plotted.

Figure 6:
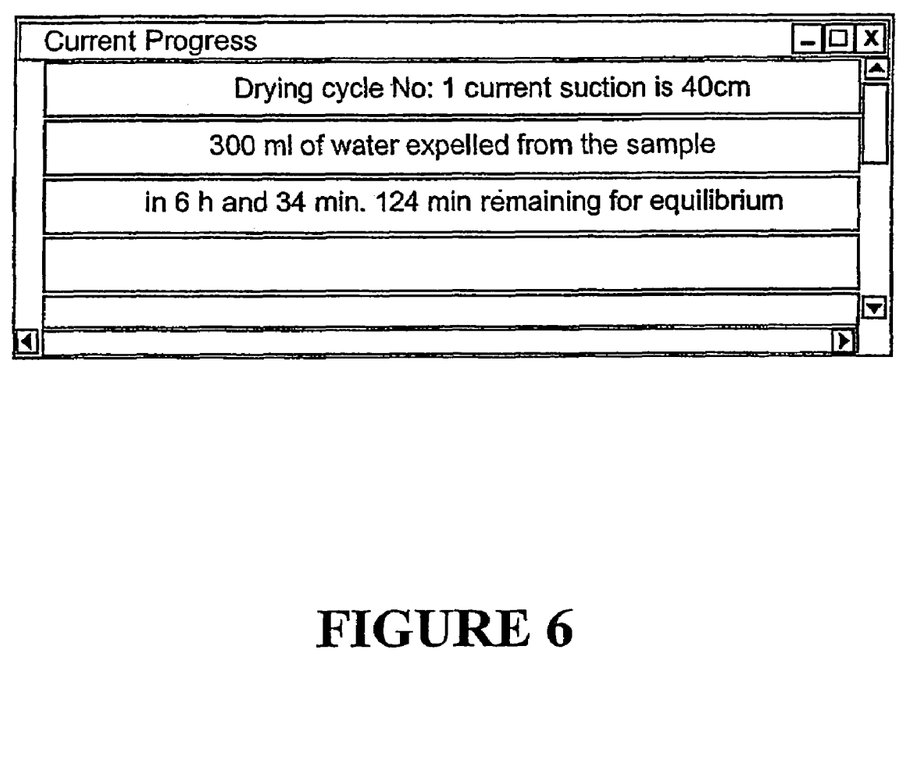
FIG. 6 shows a status panel forming part of the interface of FIG. 3.

Referring to FIG. 3, panel 308 could include a "Current Progress" button Clicking this button presents to a user a status panel such as that shown in FIG. 6. This window displays the current progress of the system such as the number of cycles being completed, current tension, and the time spent waiting for the next water segment to be filled or emptied since the last segment was detected.

As an alternative to a "Current Progress" button the display could periodically toggle between screens.

Figure 7:
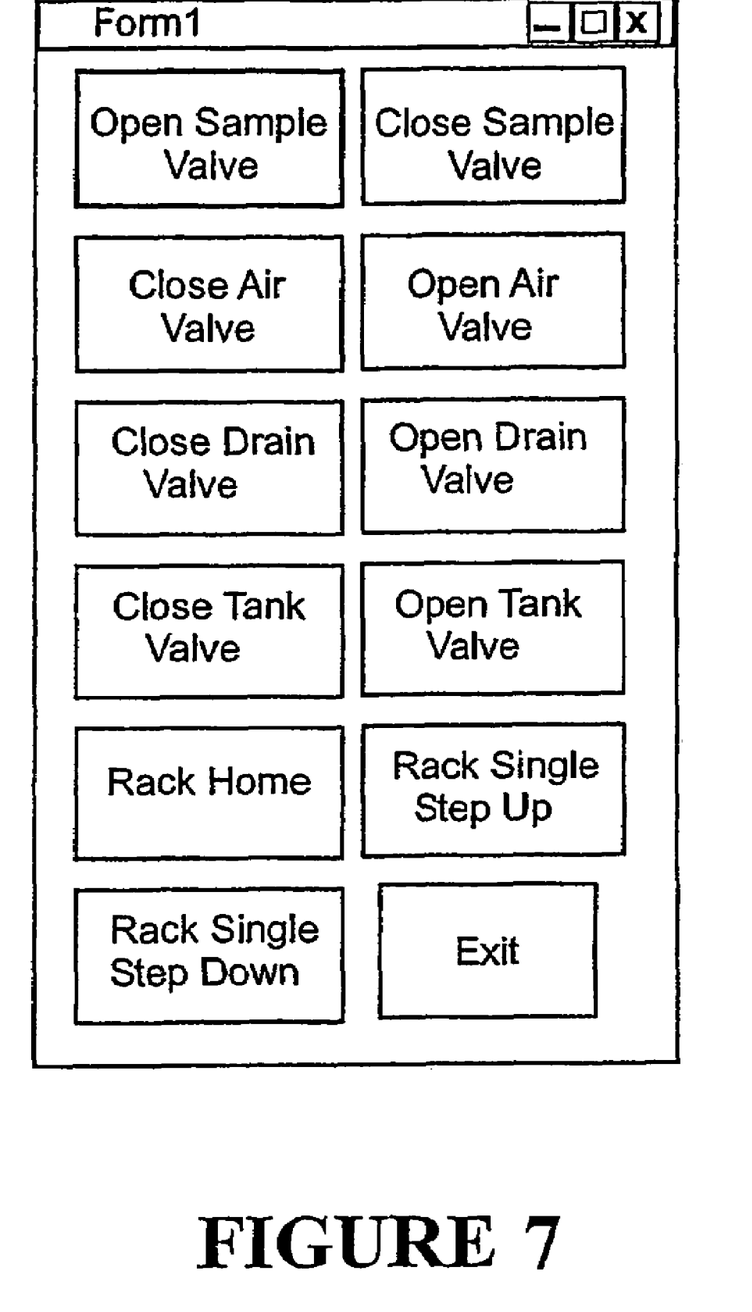
FIG. 7 shows a manual control button forming part of the interface of FIG. 3.

Referring to FIG. 3, the panel 308 may also include a manual control button 316. Clicking this button presents to a user a control panel such as that shown in FIG. 7 enabling a user to manually control parameters of the system, for example close or open the sample valve, close or open the air valve, close or open the drain valve, close or open the tank valve. The user may also return the measuring tube 160 or rack to a default position or may raise or lower the capillary tube.

Figure 8:
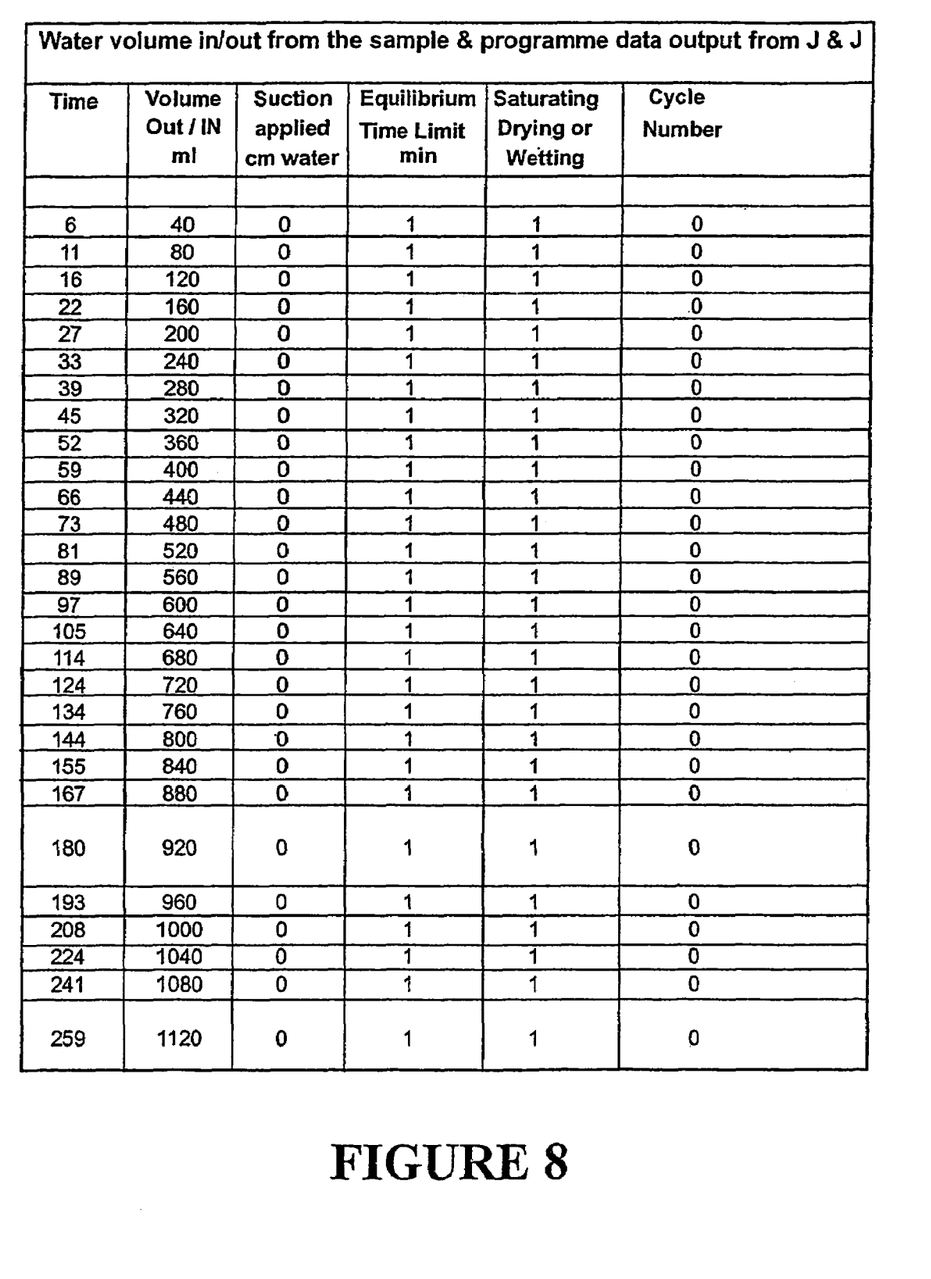
FIG. 8 illustrates sample raw data from the system of FIG. 1.

FIG. 8 shows sample raw data transferred from the apparatus 180 to the computer 190. The data could include program parameters, as a series of descriptive text strings followed by parameter values, and status data. Each data string could include, for example, hour, minute, second, cycle description (for example saturation/purging cycle, drying cycle or wetting cycle), tension value, cycle number, and cumulative volume as a number of segments.

The software running on the computer 190 could also be configured to generate a series of graphs representing the data retrieved from the apparatus 180.

Figure 9:
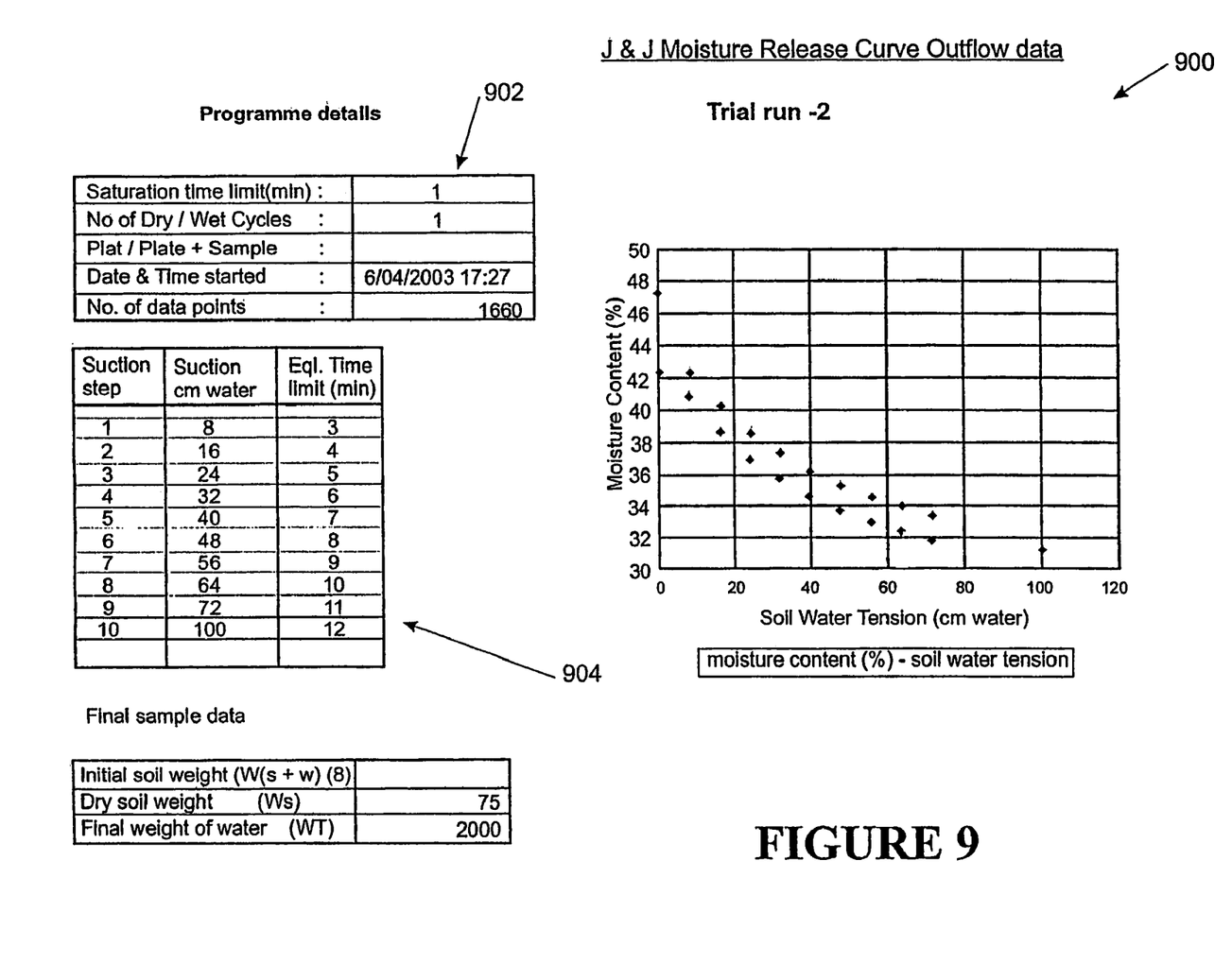
FIG. 9 shows a typical soil moisture release curve.

FIG. 9 shows a sample moisture release curve 900 produced from the outflow data downloaded in FIG. 8. The program parameters 902 and 904 are also written when the data file is saved.

The moisture release curve calculation system and method of the invention has the advantage that data is stored automatically in a programmable computing device, for example a micro controller EEPROM non-volatile memory. Data will remain in the memory of the apparatus 180 after the power is switched off and can be transferred to the computer 190 at any time. The major advantage of this system and method is that the soil sample 50 is not disturbed during measurement resulting in greater accuracy.

The foregoing describes the invention including preferred forms thereof. Alterations and modifications as will be obvious to those skilled in the art are intended to be incorporated within the scope hereof as defined by the accompanying claims.

The invention claimed is:

1. A soil moisture content measurement system comprising:
    a porous plate arranged to support a soil sample;
    a hanging water tube extending downwardly from the porous plate, the tube arranged to convey liquid toward and away from the porous plate;
    a measuring capillary tube in connection with the hanging water tube, the measuring capillary tube arranged to convey liquid toward and away from the hanging water tube, the measuring capillary tube arranged to be raised and/or lowered with respect to the soil sample;
    measurement apparatus configured to measure the movement of liquid within the measuring capillary tube; and
    a data memory configured to receive and store data from the measurement apparatus representing liquid movement measurements within the measuring capillary tube.

2. A soil moisture content measurement system as claimed in claim 1 further comprising a microcontroller associated with the data memory, the microcontroller configured to monitor the movement of liquid in the measuring capillary tube and control movement of liquid between the hanging water tube and the measuring capillary tube by raising or lowering the measuring capillary tube with respect to the soil sample.

3. A soil moisture content measurement system as claimed in claim 2 wherein the data memory and microcontroller are connectable to a computer device.

4. A soil moisture content measurement system as claimed in claim 3 wherein data stored in the data memory is transferable to the computer device.

5. A soil moisture content measurement system as claimed in claim 3 wherein commands are transferred from the computer device to the microcontroller.

6. A soil moisture content measurement system as claimed in claim 1 wherein the porous plate is elevated with respect to the measuring capillary tube.

7. A soil moisture content measurement system as claimed in claim 1 further comprising:
- a liquid receptacle elevated with respect to the hanging water tube and/or the measuring capillary tube; and
- a supply tube extending downwardly from the liquid receptacle, the tube in connection with and arranged to convey liquid to the hanging water tube and/or the measuring capillary tube.

8. A soil moisture content measurement system as claimed in claim 1 wherein the measurement apparatus comprises a series of infrared emitter and infrared detector pairs spaced along the measuring capillary tube.

9. A method of measuring a moisture retention curve of a soil sample comprising the steps of:
- supporting a soil sample on a porous plate;
- positioning the height of a measuring capillary tube with respect to the porous plate to enable liquid to be conveyed between the measuring capillary tube and the porous plate;
- positioning a hanging water tube to convey liquid between the porous plate and the measuring capillary tube;
- performing at least one purging cycle in which liquid is introduced into the measuring capillary tube and the soil sample;
- performing at least one drying cycle in which the measuring capillary tube is substantially emptied of liquid, liquid is permitted to travel from the soil sample through the porous plate to the measuring capillary tube, and the movement of liquid within the measuring capillary tube is measured;
- storing in computer memory data representing liquid movement measurements e measuring capillary tube; and
- calculating the moisture retention curve from the data representing liquid movement measurements.

10. A method of measuring a moisture retention curve as claimed in claim 9 further comprising the step of performing, after the or each drying cycle, one or more wetting cycles in which liquid is permitted to travel from the measuring capillary tube through the porous plate to the soil sample, and the movement of liquid within the measuring capillary tube is measured.

11. A method of measuring a moisture retention curve as claimed in claim 10 further comprising the step of periodically introducing liquid into the measuring capillary tube once the tube is substantially empty of liquid.

12. A method of measuring a moisture retention curve as claimed in claim 10 further comprising the step of terminating the or each wetting cycle on detection of substantially no movement of liquid within the measuring capillary tube during a predefined time limit.

13. A method of measuring a moisture retention curve as claimed in claim 10 further comprising the step of terminating the or each wetting cycle on user input.

14. A method of measuring a moisture retention curve as claimed in claim 9 further comprising the step of periodically substantially emptying the measuring capillary tube of liquid during the drying cycle once the volume of liquid within the measuring capillary tube reaches a predefined maximum.

15. A method of measuring a moisture retention curve as claimed in claim 9 further comprising the step of terminating the or each drying cycle on detection of substantially no movement of liquid within the measuring capillary tube during a predefined time limit.

16. A method of measuring a moisture retention curve as claimed in claim 9 further comprising the step of terminating the or each drying cycle on user input.

* * * * *

UNITED STATES PATENT AND TRADEMARK OFFICE
CERTIFICATE OF CORRECTION

PATENT NO. : 7,222,519 B2  Page 1 of 1
APPLICATION NO. : 10/518282
DATED : May 29, 2007
INVENTOR(S) : Jagath C. Ekanayake It is certified that error appears in the above-identified patent and that said Letters Patent is hereby corrected as shown below:

In the Claims:

At Column 9, line 14, "steps of." should be -- steps of: --.

At Column 9, line 33, "measurements e measuring" should be -- measurements within the measuring --.

Signed and Sealed this

Thirteenth Day of November, 2007

JON W. DUDAS
*Director of the United States Patent and Trademark Office*